(12) United States Patent
Donoho et al.

(10) Patent No.: US 6,852,521 B2
(45) Date of Patent: Feb. 8, 2005

(54) HUMAN PROTEASES AND POLYNUCLEOTIDES ENCODING THE SAME

(75) Inventors: Gregory Donoho, Portage, MI (US); C. Alexander Turner, Jr., The Woodlands, TX (US); Glenn Friedrich, Houston, TX (US); John Scoville, Houston, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 10/419,276

(22) Filed: Apr. 17, 2003

(65) Prior Publication Data

US 2003/0225258 A1 Dec. 4, 2003

Related U.S. Application Data

(63) Continuation of application No. 09/963,791, filed on Dec. 8, 2000, now Pat. No. 6,649,399.
(60) Provisional application No. 60/169,769, filed on Dec. 9, 1999.

(51) Int. Cl.[7] .......................... C12N 9/64; C12P 21/06; C07H 21/04

(52) U.S. Cl. ...................... 435/226; 435/69.1; 536/23.2

(58) Field of Search ............................... 435/226, 69.1; 536/23.2, 24.31, 23.1

(56) References Cited

U.S. PATENT DOCUMENTS

| | | | |
|---|---|---|---|
| 4,215,051 A | 7/1980 | Schroeder et al. | |
| 4,376,110 A | 3/1983 | David et al. | |
| 4,594,595 A | 6/1986 | Struckman | |
| 4,631,211 A | 12/1986 | Houghten | |
| 4,689,405 A | 8/1987 | Frank et al. | |
| 4,713,326 A | 12/1987 | Dattagupta et al. | |
| 4,946,778 A | 8/1990 | Ladner et al. | |
| 5,252,743 A | 10/1993 | Barrett et al. | |
| 5,424,186 A | 6/1995 | Fodor et al. | |
| 5,445,934 A | 8/1995 | Fodor et al. | |
| 5,556,752 A | 9/1996 | Lockhart et al. | |
| 5,700,637 A | 12/1997 | Southern | |
| 5,744,305 A | 4/1998 | Fodor et al. | |
| 5,830,721 A | 11/1998 | Stemmer et al. | |
| 5,837,458 A | 11/1998 | Minshull et al. | |
| 5,869,336 A | 2/1999 | Meyer et al. | |
| 5,877,397 A | 3/1999 | Lonberg et al. | |
| 5,948,767 A | 9/1999 | Scheule et al. | |
| 6,075,181 A | 6/2000 | Kucherlapati et al. | |
| 6,110,490 A | 8/2000 | Thierry | |
| 6,649,399 B2 * | 11/2003 | Donoho et al. .......... | 435/252.3 |

OTHER PUBLICATIONS

Hurskainen T.L. et al. (ADAM–TS5, ADAM–TS6, and ADAM–TS7, novel members of a new family of zinc metalloproteases. General features and genomic distribution of the ADAM–TS family, J. Biol. Chem. 1999, 274, 25555–25563).*
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.
Greenspan et al, 1993, "Idiotypes: structure and immunogenicity", FASEB Journal 7:437–444.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the lpp gene of *Escherichia coli*", Nucleic Acids Research 13(9):3101–3110.
Janknecht et al, 1991, "Rapid and efficient purification of native histidine–tagged protein expressed by recombinant vaccinia virus", PNAS 88:8972–8976.
Kohler & Milstein, 1975, "Continuous cultures of fused cells secreting antibody of predefined specificity", Nature 256:495–497.
Logan et al, 1984, "Adenovirus tripartite leader sequence enhances translation of mRNAs late after infection", Proc. Natl. Acad. Sci. USA 81:3655–3659.
Lowy et al, 1980, "Isolation of Transforming DNA: Cloning the Hamster aprt Gene", Cell 22:817–823.
Morrison et al, 1984, "Chimeric human antibody molecules: Mouse antigen–binding domains with human constant region domains", Proc. Natl. Acad. Sci. USA 81:6851–6855.

(List continued on next page.)

*Primary Examiner*—Rebecca E. Prouty
*Assistant Examiner*—Malgorzata A. Walicka

(57) ABSTRACT

Novel human polynucleotide and polypeptide sequences are disclosed that can be used in therapeutic, diagnostic, and pharmacogenomic applications.

1 Claim, No Drawings

OTHER PUBLICATIONS

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV, DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplitiable dominant–acting gene", Proc. Natl. Acad. Sci. USA 77(6):3567–3570.

Hurskainen, T.L. et al., "ADAM–TS5, ADAM–TS6, and ADAM–TS7, Novel Members of a New Family of Zinc Metalloproteases," Journal of Biological Chemistry, 274(36):25555–25563.

Tang, B.L. et al., "ADAMTS: A Novel family of proteases with an ADAM protease domain and thrombospondin 1 repeats," FEBS Letters, vol. 445, No. 2–3, 223–225.

* cited by examiner

SEQUENCE LISTING

<160> NUMBER OF SEQ ID NOS: 25

<210> SEQ ID NO 1
<211> LENGTH: 2727
<212> TYPE: DNA
<213> ORGANISM: Homo sapiens

<400> SEQUENCE: 1

| | | | | | |
|---|---|---|---|---|---|
| atggaaattt | tgtggaagac | gttgacctgg | attttgagcc | tcatcatggc | ttcatcggaa | 60 |
| tttcatagtg | accacaggct | ttcatacagt | tctcaagagg | aattcctgac | ttatcttgaa | 120 |
| cactaccagc | taactattcc | aataagggtt | gatcaaaatg | gagcatttct | cagctttact | 180 |
| gtgaaaaatg | ataaacactc | aaggagaaga | cggagtatgg | accctattga | tccacagcag | 240 |
| gcagtatcta | agttattttt | taaactttca | gcctatggca | agcactttca | tctaaacttg | 300 |
| actctcaaca | cagattttgt | gtccaaacat | tttacagtag | aatattgggg | gaaagatgga | 360 |
| ccccagtgga | aacatgattt | tttagacaac | tgtcattaca | caggatattt | gcaagatcaa | 420 |
| cgtagtacaa | ctaaagtggc | tttaagcaac | tgtgttgggt | tgcatggtgt | tattgctaca | 480 |
| gaagatgaag | agtattttat | cgaacccttta | aagaatacca | cagaggattc | caagcatttt | 540 |
| agttatgaaa | atggccaccc | tcatgttatt | tacaaaaagt | ctgcccttca | acaacgacat | 600 |
| ctgtatgatc | actctcattg | tggggtttcg | gatttcacaa | gaagtggcaa | accttggtgg | 660 |
| ctgaatgaca | catccactgt | ttcttattca | ctaccaatta | caacacacat | atccaccac | 720 |
| agacagaaga | gatcagtgag | cattgaacgg | tttgtggaga | cattggtagt | ggcagacaaa | 780 |
| atgatggtgg | gctaccatgg | ccgcaaagac | attgaacatt | acattttgag | tgtgatgaat | 840 |
| attgttgcca | aactttaccg | tgattccagc | ctaggaaacg | ttgtgaatat | tatagtggcc | 900 |
| cgcttaattg | ttctcacaga | agatcagcca | aacttggaga | taaaccacca | tgcagacaag | 960 |
| tccctcgata | gcttctgtaa | atggcagaaa | tccattctct | cccaccaaag | tgatggaaac | 1020 |
| accattccag | aaaatgggat | tgcccaccac | gataatgcag | ttcttattac | tagatatgat | 1080 |
| atctgcactt | ataaaaataa | gccctgtgga | acactgggct | tggcctctgt | ggctggaatg | 1140 |
| tgtgagcctg | aaaggagctg | cagcattaat | gaagacattg | gcctgggttc | agcttttacc | 1200 |
| attgcacatg | agattggtca | caattttggt | atgaaccatg | atggaattgg | aaattcttgt | 1260 |
| gggacgaaag | gtcatgaagc | agcaaaaactt | atggcagctc | acattactgc | gaataccaat | 1320 |
| cctttttcct | ggtctgcttg | cagtcgagac | tacatcacca | gctttctaga | ttcaggccgt | 1380 |
| ggtacttgcc | ttgataatga | gcctcccaag | cgtgactttc | tttatccagc | tgtggcccca | 1440 |
| ggtcaggtgt | atgatgctga | tgagcaatgt | cgtttccagt | atggagcaac | ctcccgccaa | 1500 |
| tgtaaaatatg | gggaagtgtg | tagagagctc | tggtgtctca | gcaaaagcaa | ccgctgtgtc | 1560 |
| accaacagta | ttccagcagc | tgaggggaca | ctgtgtcaaa | ctgggaatat | tgaaaaaggg | 1620 |
| tggtgttatc | agggagattg | tgttcctttt | ggcacttggc | cccagagcat | agatggggc | 1680 |
| tggggtccct | ggtcactatg | gggagagtgc | agcaggacct | cgggggagg | cgtctccctca | 1740 |
| tccctaagac | actgtgacag | tccagcacct | tcaggaggtg | aaaatattg | ccttggggaa | 1800 |
| aggaaacggt | atcgctcctg | taacacagat | ccatgccctt | tgggttcccg | agattttcga | 1860 |
| gagaaacagt | gtgcagactt | tgacaatatg | ccttttcgag | aaagtatta | taactggaaa | 1920 |
| ccctatactg | gaggtgggt | aaaaccttgt | gcattaaact | gcttggctga | aggttataat | 1980 |
| ttctacactg | aacgtgctcc | tgcggtgatc | gatgggaccc | agtgcaatgc | ggattcactg | 2040 |

```
gatatctgca tcaatggaga atgcaagcac gtaggctgtg ataatatttt gggatctgat    2100
gctagggaag atagatgtcg agtctgtgga ggggacggaa gcacatgtga tgccattgaa    2160
gggttcttca atgattcact gcccagggga ggctacatgg aagtggtgca gataccaaga    2220
ggctctgttc acattgaagt tagagaagtt gccatgtcaa agaactatat tgctttaaaa    2280
tctgaaggag atgattacta tattaatggt gcctggacta ttgactggcc taggaaattt    2340
gatgttgctg ggacagcttt tcattacaag agaccaactg atgaaccaga atccttggaa    2400
gctctaggtc ctacctcaga aaatctcatc gtcatggttc tgcttcaaga acagaatttg    2460
ggaattaggt ataagttcaa tgttcccatc actcgaactg gcagtggaga taatgaagtt    2520
ggctttacat ggaatcatca gccttggtca gaatgctcag ctacttgtgc tggaggtaag    2580
atgcccacta ggcagcccac ccagagggca agatggagaa caaaacacat tctgagctat    2640
gctttgtgtt tgttaaaaaa gctaattgga aacatttctt gcaggtttgc ttcaagctgt    2700
aatttagcaa agaaactttg ctttaa                                        2727
```

<210> SEQ ID NO 2
<211> LENGTH: 908
<212> TYPE: PRT
<213> ORGANISM: Homo sapiens

<400> SEQUENCE: 2

```
Met Glu Ile Leu Trp Lys Thr Leu Thr Trp Ile Leu Ser Leu Ile Met
  1               5                  10                  15

Ala Ser Ser Glu Phe His Ser Asp His Arg Leu Ser Tyr Ser Ser Gln
             20                  25                  30

Glu Glu Phe Leu Thr Tyr Leu Glu His Tyr Gln Leu Thr Ile Pro Ile
         35                  40                  45

Arg Val Asp Gln Asn Gly Ala Phe Leu Ser Phe Thr Val Lys Asn Asp
     50                  55                  60

Lys His Ser Arg Arg Arg Ser Met Asp Pro Ile Asp Pro Gln Gln
 65                  70                  75                  80

Ala Val Ser Lys Leu Phe Phe Lys Leu Ser Ala Tyr Gly Lys His Phe
                 85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
        115                 120                 125

Asp Asn Cys His Tyr Thr Gly Tyr Leu Gln Asp Gln Arg Ser Thr Thr
    130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
        195                 200                 205

Val Ser Asp Phe Thr Arg Ser Gly Lys Pro Trp Trp Leu Asn Asp Thr
    210                 215                 220

Ser Thr Val Ser Tyr Ser Leu Pro Ile Asn Asn Thr His Ile His His
225                 230                 235                 240

Arg Gln Lys Arg Ser Val Ser Ile Glu Arg Phe Val Glu Thr Leu Val
```

-continued

```
                    245                 250                 255
Val Ala Asp Lys Met Met Val Gly Tyr His Gly Arg Lys Asp Ile Glu
                260                 265                 270
His Tyr Ile Leu Ser Val Met Asn Ile Val Ala Lys Leu Tyr Arg Asp
                275                 280                 285
Ser Ser Leu Gly Asn Val Val Asn Ile Ile Val Ala Arg Leu Ile Val
            290                 295                 300
Leu Thr Glu Asp Gln Pro Asn Leu Glu Ile Asn His His Ala Asp Lys
305                 310                 315                 320
Ser Leu Asp Ser Phe Cys Lys Trp Gln Lys Ser Ile Leu Ser His Gln
                325                 330                 335
Ser Asp Gly Asn Thr Ile Pro Glu Asn Gly Ile Ala His His Asp Asn
                340                 345                 350
Ala Val Leu Ile Thr Arg Tyr Asp Ile Cys Thr Tyr Lys Asn Lys Pro
                355                 360                 365
Cys Gly Thr Leu Gly Leu Ala Ser Val Ala Gly Met Cys Glu Pro Glu
            370                 375                 380
Arg Ser Cys Ser Ile Asn Glu Asp Ile Gly Leu Gly Ser Ala Phe Thr
385                 390                 395                 400
Ile Ala His Glu Ile Gly His Asn Phe Gly Met Asn His Asp Gly Ile
                405                 410                 415
Gly Asn Ser Cys Gly Thr Lys Gly His Glu Ala Ala Lys Leu Met Ala
                420                 425                 430
Ala His Ile Thr Ala Asn Thr Asn Pro Phe Ser Trp Ser Ala Cys Ser
                435                 440                 445
Arg Asp Tyr Ile Thr Ser Phe Leu Asp Ser Gly Arg Gly Thr Cys Leu
            450                 455                 460
Asp Asn Glu Pro Pro Lys Arg Asp Phe Leu Tyr Pro Ala Val Ala Pro
465                 470                 475                 480
Gly Gln Val Tyr Asp Ala Asp Glu Gln Cys Arg Phe Gln Tyr Gly Ala
                485                 490                 495
Thr Ser Arg Gln Cys Lys Tyr Gly Glu Val Cys Arg Glu Leu Trp Cys
                500                 505                 510
Leu Ser Lys Ser Asn Arg Cys Val Thr Asn Ser Ile Pro Ala Ala Glu
            515                 520                 525
Gly Thr Leu Cys Gln Thr Gly Asn Ile Glu Lys Gly Trp Cys Tyr Gln
            530                 535                 540
Gly Asp Cys Val Pro Phe Gly Thr Trp Pro Gln Ser Ile Asp Gly Gly
545                 550                 555                 560
Trp Gly Pro Trp Ser Leu Trp Gly Glu Cys Ser Arg Thr Cys Gly Gly
                565                 570                 575
Gly Val Ser Ser Ser Leu Arg His Cys Asp Ser Pro Ala Pro Ser Gly
                580                 585                 590
Gly Gly Lys Tyr Cys Leu Gly Glu Arg Lys Arg Tyr Arg Ser Cys Asn
                595                 600                 605
Thr Asp Pro Cys Pro Leu Gly Ser Arg Asp Phe Arg Glu Lys Gln Cys
            610                 615                 620
Ala Asp Phe Asp Asn Met Pro Phe Arg Gly Lys Tyr Tyr Asn Trp Lys
625                 630                 635                 640
Pro Tyr Thr Gly Gly Gly Val Lys Pro Cys Ala Leu Asn Cys Leu Ala
                645                 650                 655
Glu Gly Tyr Asn Phe Tyr Thr Glu Arg Ala Pro Ala Val Ile Asp Gly
                660                 665                 670
```

```
Thr Gln Cys Asn Ala Asp Ser Leu Asp Ile Cys Ile Asn Gly Glu Cys
        675                 680                 685
Lys His Val Gly Cys Asp Asn Ile Leu Gly Ser Asp Ala Arg Glu Asp
        690                 695                 700
Arg Cys Arg Val Cys Gly Gly Asp Gly Ser Thr Cys Asp Ala Ile Glu
705                 710                 715                 720
Gly Phe Phe Asn Asp Ser Leu Pro Arg Gly Tyr Met Glu Val Val
                725                 730                 735
Gln Ile Pro Arg Gly Ser Val His Ile Glu Val Arg Glu Val Ala Met
            740                 745                 750
Ser Lys Asn Tyr Ile Ala Leu Lys Ser Glu Gly Asp Asp Tyr Tyr Ile
            755                 760                 765
Asn Gly Ala Trp Thr Ile Asp Trp Pro Arg Lys Phe Asp Val Ala Gly
            770                 775                 780
Thr Ala Phe His Tyr Lys Arg Pro Thr Asp Glu Pro Glu Ser Leu Glu
785                 790                 795                 800
Ala Leu Gly Pro Thr Ser Glu Asn Leu Ile Val Met Val Leu Leu Gln
                805                 810                 815
Glu Gln Asn Leu Gly Ile Arg Tyr Lys Phe Asn Val Pro Ile Thr Arg
            820                 825                 830
Thr Gly Ser Gly Asp Asn Glu Val Gly Phe Thr Trp Asn His Gln Pro
            835                 840                 845
Trp Ser Glu Cys Ser Ala Thr Cys Ala Gly Gly Lys Met Pro Thr Arg
850                 855                 860
Gln Pro Thr Gln Arg Ala Arg Trp Arg Thr Lys His Ile Leu Ser Tyr
865                 870                 875                 880
Ala Leu Cys Leu Leu Lys Lys Leu Ile Gly Asn Ile Ser Cys Arg Phe
            885                 890                 895
Ala Ser Ser Cys Asn Leu Ala Lys Glu Thr Leu Leu
            900                 905

<210> SEQ ID NO 3
<211> LENGTH: 879
<212> TYPE: DNA
<213> ORGANISM: Homo sapiens

<400> SEQUENCE: 3
atggaaattt tgtggaagac gttgacctgg attttgagcc tcatcatggc ttcatcggaa      60
tttcatagtg accacaggct ttcatacagt tctcaagagg aattcctgac ttatcttgaa     120
cactaccagc taactattcc aataagggtt gatcaaaatg gagcatttct cagctttact     180
gtgaaaaatg ataaacactc aaggagaaga cggagtatgg accctattga tccacagcag     240
gcagtatcta agttattttt taaactttca gcctatggca agcactttca tctaaacttg     300
actctcaaca cagattttgt gtccaaacat tttacagtag aatattgggg gaaagatgga     360
ccccagtgga acatgatttt ttagacaac tgtcattaca caggatattt gcaagatcaa     420
cgtagtacaa ctaaagtggc tttaagcaac tgtgttgggt tgcatggtgt tattgctaca     480
gaagatgaag agtattttat cgaacccttta aagaatacca cagaggattc caagcatttt     540
agttatgaaa atggccaccc tcatgttatt tacaaaaagt ctgcccttca caacgacat     600
ctgtatgatc actctcattg tggggtttcg gatttcacaa gaagtggcaa accttggtgg     660
ctgaatgaca catccactgt ttcttattca ctaccaatta caacacaca tatccaccac     720
agacagaaga gatcagtgag cattgaacgg tttgtggaga cattggtagt ggcagacaaa     780
```
atgatggtgg gctaccatgg ccgcaaagac attgaacatt acattttgag tgtgatgaat    840
attgtcaggt tgccaaactt taccgtgatt ccagcctag    879

<210> SEQ ID NO 4
<211> LENGTH: 292
<212> TYPE: PRT
<213> ORGANISM: Homo sapiens

<400> SEQUENCE: 4

Met Glu Ile Leu Trp Lys Thr Leu Thr Trp Ile Leu Ser Leu Ile Met
1               5                   10                  15

Ala Ser Ser Glu Phe His Ser Asp His Arg Leu Ser Tyr Ser Ser Gln
            20                  25                  30

Glu Glu Phe Leu Thr Tyr Leu Glu His Tyr Gln Leu Thr Ile Pro Ile
        35                  40                  45

Arg Val Asp Gln Asn Gly Ala Phe Leu Ser Phe Thr Val Lys Asn Asp
    50                  55                  60

Lys His Ser Arg Arg Arg Ser Met Asp Pro Ile Asp Pro Gln Gln
65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
        115                 120                 125

Asp Asn Cys His Tyr Thr Gly Tyr Leu Gln Asp Gln Arg Ser Thr Thr
    130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
        195                 200                 205

Val Ser Asp Phe Thr Arg Ser Gly Lys Pro Trp Trp Leu Asn Asp Thr
    210                 215                 220

Ser Thr Val Ser Tyr Ser Leu Pro Ile Asn Asn Thr His Ile His His
225                 230                 235                 240

Arg Gln Lys Arg Ser Val Ser Ile Glu Arg Phe Val Glu Thr Leu Val
                245                 250                 255

Val Ala Asp Lys Met Met Val Gly Tyr His Gly Arg Lys Asp Ile Glu
            260                 265                 270

His Tyr Ile Leu Ser Val Met Asn Ile Val Arg Leu Pro Asn Phe Thr
        275                 280                 285

Val Ile Pro Ala
    290

<210> SEQ ID NO 5
<211> LENGTH: 1407
<212> TYPE: DNA
<213> ORGANISM: Homo sapiens

<400> SEQUENCE: 5
atggaaattt tgtggaagac gttgacctgg attttgagcc tcatcatggc ttcatcggaa    60

```
tttcatagtg accacaggct ttcatacagt tctcaagagg aattcctgac ttatcttgaa      120
cactaccagc taactattcc aataagggtt gatcaaaatg gagcatttct cagctttact      180
gtgaaaaatg ataaacactc aaggagaaga cggagtatgg accctattga tccacagcag      240
gcagtatcta agttatttt taaactttca gcctatggca agcactttca tctaaacttg       300
actctcaaca cagattttgt gtccaaacat tttacagtag aatattgggg gaaagatgga      360
ccccagtgga aacatgattt tttagacaac tgtcattaca caggatattt gcaagatcaa      420
cgtagtacaa ctaaagtggc tttaagcaac tgtgttgggt tgcatggtgt tattgctaca      480
gaagatgaag agtattttat cgaacctta aagaatacca cagaggattc caagcatttt       540
agttatgaaa atggccaccc tcatgttatt tacaaaaagt ctgcccttca acaacgacat      600
ctgtatgatc actctcattg tggggtttcg gatttcacaa gaagtggcaa accttggtgg     660
ctgaatgaca catccactgt ttcttattca ctaccaatta caacacacac tatccaccac      720
agacagaaga gatcagtgag cattgaacgg tttgtggaga cattggtagt ggcagacaaa      780
atgatggtgg gctaccatgg ccgcaaagac attgaacatt acattttgag tgtgatgaat      840
attgttgcca aactttaccg tgattccagc ctaggaaacg ttgtgaatat tatagtggcc     900
cgcttaattg ttctcacaga agatcagcca aacttggaga taaaccacca tgcagacaag      960
tccctcgata gcttctgtaa atggcagaaa tccattctct cccaccaaag tgatggaaac     1020
accattccag aaaatgggat tgcccaccac gataatgcag ttcttattac tagatatgat     1080
atctgcactt ataaaaataa gccctgtgga acactgggct tggcctctgt ggctggaatg     1140
tgtgagcctg aaaggagctg cagcattaat gaagacattg gcctgggttc agcttttacc     1200
attgcacatg agattggtca aattttggt atgaaccatg atggaattgg aaattcttgt      1260
gggacgaaag gtcatgaagc agcaaaactt atggcagctc acattactgc gaataccaat     1320 ccttttttcct ggtctgcttg cagtcgagac tacatcacca gctttctaga atttcttaaa    1380
ctcggtgatt caataagtgg ttcatga                                         1407
```

<210> SEQ ID NO 6
<211> LENGTH: 468
<212> TYPE: PRT
<213> ORGANISM: Homo sapiens

<400> SEQUENCE: 6

```
Met Glu Ile Leu Trp Lys Thr Leu Thr Trp Ile Leu Ser Leu Ile Met
 1               5                  10                  15

Ala Ser Ser Glu Phe His Ser Asp His Arg Leu Ser Tyr Ser Ser Gln
            20                  25                  30

Glu Glu Phe Leu Thr Tyr Leu Glu His Tyr Gln Leu Thr Ile Pro Ile
        35                  40                  45

Arg Val Asp Gln Asn Gly Ala Phe Leu Ser Phe Thr Val Lys Asn Asp
    50                  55                  60

Lys His Ser Arg Arg Arg Ser Met Asp Pro Ile Asp Pro Gln Gln
65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
        115                 120                 125
```

-continued

```
Asp Asn Cys His Tyr Thr Gly Tyr Leu Gln Asp Gln Arg Ser Thr Thr
130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
                180                 185                 190

Lys Ser Ala Leu Gln Gln Arg His Leu Tyr Asp His Ser His Cys Gly
                195                 200                 205

Val Ser Asp Phe Thr Arg Ser Gly Lys Pro Trp Trp Leu Asn Asp Thr
210                 215                 220

Ser Thr Val Ser Tyr Ser Leu Pro Ile Asn Asn Thr His Ile His His
225                 230                 235                 240

Arg Gln Lys Arg Ser Val Ser Ile Glu Arg Phe Val Glu Thr Leu Val
                245                 250                 255

Val Ala Asp Lys Met Met Val Gly Tyr His Gly Arg Lys Asp Ile Glu
                260                 265                 270

His Tyr Ile Leu Ser Val Met Asn Ile Val Ala Lys Leu Tyr Arg Asp
                275                 280                 285

Ser Ser Leu Gly Asn Val Val Asn Ile Ile Val Ala Arg Leu Ile Val
290                 295                 300

Leu Thr Glu Asp Gln Pro Asn Leu Glu Ile Asn His His Ala Asp Lys
305                 310                 315                 320

Ser Leu Asp Ser Phe Cys Lys Trp Gln Lys Ser Ile Leu Ser His Gln
                325                 330                 335

Ser Asp Gly Asn Thr Ile Pro Glu Asn Gly Ile Ala His His Asp Asn
                340                 345                 350

Ala Val Leu Ile Thr Arg Tyr Asp Ile Cys Thr Tyr Lys Asn Lys Pro
                355                 360                 365

Cys Gly Thr Leu Gly Leu Ala Ser Val Ala Gly Met Cys Glu Pro Glu
370                 375                 380

Arg Ser Cys Ser Ile Asn Glu Asp Ile Gly Leu Gly Ser Ala Phe Thr
385                 390                 395                 400

Ile Ala His Glu Ile Gly His Asn Phe Gly Met Asn His Asp Gly Ile
                405                 410                 415

Gly Asn Ser Cys Gly Thr Lys Gly His Glu Ala Ala Lys Leu Met Ala
                420                 425                 430

Ala His Ile Thr Ala Asn Thr Asn Pro Phe Ser Trp Ser Ala Cys Ser
                435                 440                 445

Arg Asp Tyr Ile Thr Ser Phe Leu Glu Phe Leu Lys Leu Gly Asp Ser
    450                 455                 460

Ile Ser Gly Ser
465

<210> SEQ ID NO 7
<211> LENGTH: 933
<212> TYPE: DNA
<213> ORGANISM: Homo sapiens

<400> SEQUENCE: 7
atggaaattt tgtggaagac gttgacctgg attttgagcc tcatcatggc ttcatcggaa       60
tttcatagtg accacaggct ttcatacagt tctcaagagg aattcctgac ttatcttgaa      120
cactaccagc taactattcc aataagggtt gatcaaaatg gagcatttct cagctttact      180
```

```
gtgaaaaatg ataaacactc aaggagaaga cggagtatgg accctattga tccacagcag    240
gcagtatcta agttattttt taaactttca gcctatggca agcactttca tctaaacttg    300
actctcaaca cagattttgt gtccaaacat tttacagtag aatattgggg gaaagatgga    360
ccccagtgga acatgatttt tttagacaac tgtcattaca caggatattt gcaagatcaa    420
cgtagtacaa ctaaagtggc tttaagcaac tgtgttgggt tgcatggtgt tattgctaca    480
gaagatgaag agtattttat cgaacccttta aagaatacca cagaggattc caagcatttt    540
agttatgaaa atggccaccc tcatgttatt tacaaaaagt ctgcccttca acaacgacat    600
ctgtatgatc actctcattg tggggtttcg gatttcacaa gaagtggcaa accttggtgg    660
ctgaatgaca catccactgt ttcttattca ctaccaatta acaacacaca tatccaccac    720
agacagaaga gatcagtgag cattgaacgg tttgtggaga cattggtagt ggcagacaaa    780
atgatggtgg gctaccatgg ccgcaaagac attgaacatt acatttttgag tgtgatgaat    840 attgttgcca aactttaccg tgattccagc ctaggaaacg ttgtgaatat tatagtggcc    900
cgcttaattg ttctcacaga agatcagata tga                                 933

<210> SEQ ID NO 8
<211> LENGTH: 310
<212> TYPE: PRT
<213> ORGANISM: Homo sapiens

<400> SEQUENCE: 8

Met Glu Ile Leu Trp Lys Thr Leu Thr Trp Ile Leu Ser Leu Ile Met
 1               5                  10                  15

Ala Ser Ser Glu Phe His Ser Asp His Arg Leu Ser Tyr Ser Ser Gln
                20                  25                  30

Glu Glu Phe Leu Thr Tyr Leu Glu His Tyr Gln Leu Thr Ile Pro Ile
            35                  40                  45

Arg Val Asp Gln Asn Gly Ala Phe Leu Ser Phe Thr Val Lys Asn Asp
        50                  55                  60

Lys His Ser Arg Arg Arg Ser Met Asp Pro Ile Asp Pro Gln Gln
 65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
        115                 120                 125

Asp Asn Cys His Tyr Thr Gly Tyr Leu Gln Asp Gln Arg Ser Thr Thr
    130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
        195                 200                 205

Val Ser Asp Phe Thr Arg Ser Gly Lys Pro Trp Trp Leu Asn Asp Thr
    210                 215                 220

Ser Thr Val Ser Tyr Ser Leu Pro Ile Asn Asn Thr His Ile His His
225                 230                 235                 240
```

-continued

Arg Gln Lys Arg Ser Val Ser Ile Glu Arg Phe Val Glu Thr Leu Val
                245                 250                 255

Val Ala Asp Lys Met Met Val Gly Tyr His Gly Arg Lys Asp Ile Glu
            260                 265                 270

His Tyr Ile Leu Ser Val Met Asn Ile Val Ala Lys Leu Tyr Arg Asp
        275                 280                 285

Ser Ser Leu Gly Asn Val Val Asn Ile Ile Val Ala Arg Leu Ile Val
    290                 295                 300

Leu Thr Glu Asp Gln Ile
305             310

<210> SEQ ID NO 9
<211> LENGTH: 1524
<212> TYPE: DNA
<213> ORGANISM: Homo sapiens

<400> SEQUENCE: 9

```
atggaaattt tgtggaagac gttgacctgg attttgagcc tcatcatggc ttcatcggaa      60
tttcatagtg accacaggct ttcatacagt tctcaagagg aattcctgac ttatcttgaa     120
cactaccagc taactattcc aataagggtt gatcaaaatg gagcatttct cagctttact     180
gtgaaaaatg ataaacactc aaggagaaga cggagtatgg accctattga tccacagcag     240
gcagtatcta gttattttt taaactttca gcctatggca agcactttca tctaaacttg     300
actctcaaca cagattttgt gtccaaacat tttacagtag aatattgggg aaagatgga      360
ccccagtgga acatgatttt ttagacaac tgtcattaca caggatattt gcaagatcaa     420
cgtagtacaa ctaaagtggc tttaagcaac tgtgttgggt tgcatggtgt tattgctaca     480
gaagatgaag agtattttat cgaacctta aagaatacca cagaggattc caagcatttt     540
agttatgaaa atggccaccc tcatgttatt tacaaaaagt ctgcccttca caacgacat      600
ctgtatgatc actctcattg tggggtttcg gatttcacaa gaagtggcaa accttggtgg     660
ctgaatgaca catccactgt ttcttattca ctaccaatta caacacaca tatccaccac     720
agacagaaga gatcagtgag cattgaacgg tttgtggaga cattggtagt ggcagacaaa     780
atgatggtgg gctaccatgg ccgcaaagac attgaacatt acattttgag tgtgatgaat     840
attgttgcca aactttaccg tgattccagc ctaggaaacg ttgtgaatat tatagtggcc     900
cgcttaattg ttctcacaga agatcagcca aacttggaga taaaccacca tgcagacaag     960
tccctcgata gcttctgtaa atggcagaaa tccattctct cccaccaaag tgatggaaac    1020
accattccag aaaatgggat tgcccaccac gataatgcag ttcttattac tagatatgat    1080
atctgcactt ataaaaataa gccctgtgga acactgggct tggcctctgt ggctggaatg    1140
tgtgagcctg aaaggagctg cagcattaat gaagacattg gcctgggttc agcttttacc    1200
attgcacatg agattggtca aattttggtt atgaaccatg atggaattgg aaattcttgt    1260
gggacgaaag gtcatgaagc agcaaaactt atggcagctc acattactgc gaataccaat    1320
cctttttcct ggtctgcttg cagtcgagac tacatcacca gctttctaga ttcaggccgt    1380
ggtacttgcc ttgataatga gcctcccaag cgtgactttc tttatccagc tgtggcccca    1440
ggtcaggtgt atgatgctga tgagcaatgt cgttccagt atggagcaac ctcccgccaa    1500
tgtaaatatg gggtctttag ataa                                            1524
```

<210> SEQ ID NO 10
<211> LENGTH: 507

<212> TYPE: PRT
<213> ORGANISM: Homo sapiens

<400> SEQUENCE: 10

```
Met Glu Ile Leu Trp Lys Thr Leu Thr Trp Ile Leu Ser Leu Ile Met
 1               5                  10                  15

Ala Ser Ser Glu Phe His Ser Asp His Arg Leu Ser Tyr Ser Ser Gln
                20                  25                  30

Glu Glu Phe Leu Thr Tyr Leu Glu His Tyr Gln Leu Thr Ile Pro Ile
            35                  40                  45

Arg Val Asp Gln Asn Gly Ala Phe Leu Ser Phe Thr Val Lys Asn Asp
 50                  55                  60

Lys His Ser Arg Arg Arg Ser Met Asp Pro Ile Asp Pro Gln Gln
 65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
            115                 120                 125

Asp Asn Cys His Tyr Thr Gly Tyr Leu Gln Asp Gln Arg Ser Thr Thr
130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
            195                 200                 205

Val Ser Asp Phe Thr Arg Ser Gly Lys Pro Trp Trp Leu Asn Asp Thr
            210                 215                 220

Ser Thr Val Ser Tyr Ser Leu Pro Ile Asn Asn Thr His Ile His His
225                 230                 235                 240

Arg Gln Lys Arg Ser Val Ser Ile Glu Arg Phe Val Glu Thr Leu Val
                245                 250                 255

Val Ala Asp Lys Met Met Val Gly Tyr His Gly Arg Lys Asp Ile Glu
            260                 265                 270

His Tyr Ile Leu Ser Val Met Asn Ile Val Ala Lys Leu Tyr Arg Asp
            275                 280                 285

Ser Ser Leu Gly Asn Val Val Asn Ile Ile Val Ala Arg Leu Ile Val
290                 295                 300

Leu Thr Glu Asp Gln Pro Asn Leu Glu Ile Asn His His Ala Asp Lys
305                 310                 315                 320

Ser Leu Asp Ser Phe Cys Lys Trp Gln Lys Ser Ile Leu Ser His Gln
                325                 330                 335

Ser Asp Gly Asn Thr Ile Pro Glu Asn Gly Ile Ala His His Asp Asn
            340                 345                 350

Ala Val Leu Ile Thr Arg Tyr Asp Ile Cys Thr Tyr Lys Asn Lys Pro
            355                 360                 365

Cys Gly Thr Leu Gly Leu Ala Ser Val Ala Gly Met Cys Glu Pro Glu
370                 375                 380

Arg Ser Cys Ser Ile Asn Glu Asp Ile Gly Leu Gly Ser Ala Phe Thr
385                 390                 395                 400
```

Ile Ala His Glu Ile Gly His Asn Phe Gly Met Asn His Asp Gly Ile
            405                 410                 415

Gly Asn Ser Cys Gly Thr Lys Gly His Glu Ala Ala Lys Leu Met Ala
            420                 425                 430

Ala His Ile Thr Ala Asn Thr Asn Pro Phe Ser Trp Ser Ala Cys Ser
            435                 440                 445

Arg Asp Tyr Ile Thr Ser Phe Leu Asp Ser Gly Arg Gly Thr Cys Leu
        450                 455                 460

Asp Asn Glu Pro Pro Lys Arg Asp Phe Leu Tyr Pro Ala Val Ala Pro
465                 470                 475                 480

Gly Gln Val Tyr Asp Ala Asp Glu Gln Cys Arg Phe Gln Tyr Gly Ala
                485                 490                 495

Thr Ser Arg Gln Cys Lys Tyr Gly Val Phe Arg
            500                 505

<210> SEQ ID NO 11
<211> LENGTH: 1770
<212> TYPE: DNA
<213> ORGANISM: Homo sapiens

<400> SEQUENCE: 11

| | | | | | |
|---|---|---|---|---|---|
| atggaaattt | tgtggaagac | gttgacctgg | attttgagcc | tcatcatggc | ttcatcggaa | 60 |
| tttcatagtg | accacaggct | ttcatacagt | tctcaagagg | aattcctgac | ttatcttgaa | 120 |
| cactaccagc | taactattcc | aataagggtt | gatcaaaatg | gagcatttct | cagctttact | 180 |
| gtgaaaaatg | ataaacactc | aaggagaaga | cggagtatgg | accctattga | tccacagcag | 240 |
| gcagtatcta | agttattttt | taaactttca | gcctatggca | agcactttca | tctaaacttg | 300 |
| actctcaaca | cagattttgt | gtccaaacat | tttacagtag | aatattgggg | gaaagatgga | 360 |
| ccccagtgga | acatgatttt | ttagacaac | tgtcattaca | caggatattt | gcaagatcaa | 420 |
| cgtagtacaa | ctaaagtggc | tttaagcaac | tgtgttgggt | gcatggtgt | tattgctaca | 480 |
| gaagatgaag | agtattttat | cgaacctta | aagaatacca | cagaggattc | caagcatttt | 540 |
| agttatgaaa | atggccaccc | tcatgttatt | tacaaaaagt | ctgcccttca | caacgacat | 600 |
| ctgtatgatc | actctcattg | tggggtttcg | gatttcacaa | gaagtggcaa | accttggtgg | 660 |
| ctgaatgaca | catccactgt | ttcttattca | ctaccaatta | caacacaca | tatccaccac | 720 |
| agacagaaga | gatcagtgag | cattgaacgg | tttgtggaga | cattggtagt | ggcagacaaa | 780 |
| atgatggtgg | gctaccatgg | ccgcaaagac | attgaacatt | acattttgag | tgtgatgaat | 840 |
| attgttgcca | aactttaccg | tgattccagc | ctaggaaacg | ttgtgaatat | tatagtggcc | 900 |
| cgcttaattg | ttctcacaga | agatcagcca | aacttggaga | taaaccacca | tgcagacaag | 960 |
| tccctcgata | gcttctgtaa | atggcagaaa | tccattctct | cccaccaaag | tgatggaaac | 1020 |
| accattccag | aaaatgggat | tgcccaccac | gataatgcag | ttcttattac | tagatatgat | 1080 |
| atctgcactt | ataaaaataa | gccctgtgga | acactgggct | tggcctctgt | ggctggaatg | 1140 |
| tgtgagcctg | aaaggagctg | cagcattaat | gaagacattg | gcctgggttc | agcttttacc | 1200 |
| attgcacatg | agattggtca | caattttggt | atgaaccatg | atggaattgg | aaattcttgt | 1260 |
| gggacgaaag | gtcatgaagc | agcaaaactt | atggcagctc | acattactgc | gaataccaat | 1320 |
| ccttttttcct | ggtctgcttg | cagtcgagac | tacatcacca | gctttctaga | ttcaggccgt | 1380 |
| ggtacttgcc | ttgataatga | gcctcccaag | cgtgactttc | tttatccagc | tgtgcccca | 1440 |
| ggtcaggtgt | atgatgctga | tgagcaatgt | cgtttccagt | atggagcaac | ctcccgccaa | 1500 |

-continued

```
tgtaaatatg gggaagtgtg tagagagctc tggtgtctca gcaaaagcaa ccgctgtgtc      1560
accaacagta ttccagcagc tgagggggaca ctgtgtcaaa ctgggaatat tgaaaaaggg     1620
tggtgttatc agggagattg tgttcctttt ggcacttggc cccagagcat agatgggggc     1680
tggggtccct ggtcactatg gggagagtgc agcaggacct gcggggagg cgtctcctca      1740 tccctaagac actgtgacag tccagcgtaa                                      1770
```

```
<210> SEQ ID NO 12
<211> LENGTH: 589
<212> TYPE: PRT
<213> ORGANISM: Homo sapiens

<400> SEQUENCE: 12

Met Glu Ile Leu Trp Lys Thr Leu Thr Trp Ile Leu Ser Leu Ile Met
 1               5                  10                  15

Ala Ser Ser Glu Phe His Ser Asp His Arg Leu Ser Tyr Ser Ser Gln
            20                  25                  30

Glu Glu Phe Leu Thr Tyr Leu Glu His Tyr Gln Leu Thr Ile Pro Ile
        35                  40                  45

Arg Val Asp Gln Asn Gly Ala Phe Leu Ser Phe Thr Val Lys Asn Asp
    50                  55                  60

Lys His Ser Arg Arg Arg Ser Met Asp Pro Ile Asp Pro Gln Gln
65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
        115                 120                 125

Asp Asn Cys His Tyr Thr Gly Tyr Leu Gln Asp Gln Arg Ser Thr Thr
    130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
        195                 200                 205

Val Ser Asp Phe Thr Arg Ser Gly Lys Pro Trp Trp Leu Asn Asp Thr
    210                 215                 220

Ser Thr Val Ser Tyr Ser Leu Pro Ile Asn Asn Thr His Ile His His
225                 230                 235                 240

Arg Gln Lys Arg Ser Val Ser Ile Glu Arg Phe Val Glu Thr Leu Val
                245                 250                 255

Val Ala Asp Lys Met Met Val Gly Tyr His Gly Arg Lys Asp Ile Glu
            260                 265                 270

His Tyr Ile Leu Ser Val Met Asn Ile Val Ala Lys Leu Tyr Arg Asp
        275                 280                 285

Ser Ser Leu Gly Asn Val Val Asn Ile Ile Val Ala Arg Leu Ile Val
    290                 295                 300

Leu Thr Glu Asp Gln Pro Asn Leu Glu Ile Asn His His Ala Asp Lys
305                 310                 315                 320
```

```
Ser Leu Asp Ser Phe Cys Lys Trp Gln Lys Ser Ile Leu Ser His Gln
            325                 330                 335

Ser Asp Gly Asn Thr Ile Pro Glu Asn Gly Ile Ala His His Asp Asn
            340                 345                 350

Ala Val Leu Ile Thr Arg Tyr Asp Ile Cys Thr Tyr Lys Asn Lys Pro
            355                 360                 365

Cys Gly Thr Leu Gly Leu Ala Ser Val Ala Gly Met Cys Glu Pro Glu
        370                 375                 380

Arg Ser Cys Ser Ile Asn Glu Asp Ile Gly Leu Gly Ser Ala Phe Thr
385                 390                 395                 400

Ile Ala His Glu Ile Gly His Asn Phe Gly Met Asn His Asp Gly Ile
                405                 410                 415

Gly Asn Ser Cys Gly Thr Lys Gly His Glu Ala Ala Lys Leu Met Ala
            420                 425                 430

Ala His Ile Thr Ala Asn Thr Asn Pro Phe Ser Trp Ser Ala Cys Ser
        435                 440                 445

Arg Asp Tyr Ile Thr Ser Phe Leu Asp Ser Gly Arg Gly Thr Cys Leu
    450                 455                 460

Asp Asn Glu Pro Pro Lys Arg Asp Phe Leu Tyr Pro Ala Val Ala Pro
465                 470                 475                 480

Gly Gln Val Tyr Asp Ala Asp Glu Gln Cys Arg Phe Gln Tyr Gly Ala
                485                 490                 495

Thr Ser Arg Gln Cys Lys Tyr Gly Glu Val Cys Arg Glu Leu Trp Cys
            500                 505                 510

Leu Ser Lys Ser Asn Arg Cys Val Thr Asn Ser Ile Pro Ala Ala Glu
        515                 520                 525

Gly Thr Leu Cys Gln Thr Gly Asn Ile Glu Lys Gly Trp Cys Tyr Gln
    530                 535                 540

Gly Asp Cys Val Pro Phe Gly Thr Trp Pro Gln Ser Ile Asp Gly Gly
545                 550                 555                 560

Trp Gly Pro Trp Ser Leu Trp Gly Glu Cys Ser Arg Thr Cys Gly Gly
                565                 570                 575

Gly Val Ser Ser Ser Leu Arg His Cys Asp Ser Pro Ala
            580                 585

<210> SEQ ID NO 13
<211> LENGTH: 426
<212> TYPE: DNA
<213> ORGANISM: Homo sapiens

<400> SEQUENCE: 13
atgaaaacgc atggtgttat tgctacagaa gatgaagagt attttatcga acctttaaag      60
aataccacag aggattccaa gcattttagt tatgaaaatg ccaccctca tgttatttac      120
aaaaagtctg cccttcaaca acgacatctg tatgatcact ctcattgtgg ggtttcggat     180
ttcacaagaa gtggcaaacc ttggtggctg aatgacacat ccactgtttc ttattcacta     240
ccaattaaca acacacatat ccaccacaga cagaagagat cagtgagcat gaacggtttt     300
gtggagacat tggtagtggc agacaaaatg atggtgggct accatggccg caaagacatt     360
gaacattaca ttttgagtgt gatgaatatt gtcaggttgc aaactttac cgtgattcca     420
gcctag                                                                426

<210> SEQ ID NO 14
<211> LENGTH: 141
<212> TYPE: PRT
```

<213> ORGANISM: Homo sapiens

<400> SEQUENCE: 14

```
Met Lys Thr His Gly Val Ile Ala Thr Glu Asp Glu Tyr Phe Ile
 1               5                  10                  15

Glu Pro Leu Lys Asn Thr Thr Glu Asp Ser Lys His Phe Ser Tyr Glu
                20                  25                  30

Asn Gly His Pro His Val Ile Tyr Lys Lys Ser Ala Leu Gln Gln Arg
            35                  40                  45

His Leu Tyr Asp His Ser His Cys Gly Val Ser Asp Phe Thr Arg Ser
50                  55                  60

Gly Lys Pro Trp Trp Leu Asn Asp Thr Ser Thr Val Ser Tyr Ser Leu
65                  70                  75                  80

Pro Ile Asn Asn Thr His Ile His Arg Gln Lys Arg Ser Val Ser
                85                  90                  95

Ile Glu Arg Phe Val Glu Thr Leu Val Val Ala Asp Lys Met Met Val
            100                 105                 110

Gly Tyr His Gly Arg Lys Asp Ile Glu His Tyr Ile Leu Ser Val Met
        115                 120                 125

Asn Ile Val Arg Leu Pro Asn Phe Thr Val Ile Pro Ala
    130                 135                 140
```

<210> SEQ ID NO 15
<211> LENGTH: 954
<212> TYPE: DNA
<213> ORGANISM: Homo sapiens

<400> SEQUENCE: 15

```
atgaaaacgc atggtgttat tgctacagaa gatgaagagt attttatcga acctttaaag      60
aataccacag aggattccaa gcattttagt tatgaaaatg ccacccctca tgttatttac     120
aaaaagtctg cccttcaaca acgacatctg tatgatcact ctcattgtgg ggtttcggat     180
ttcacaagaa gtggcaaacc ttggtggctg aatgacacat ccactgtttc ttattcacta     240
ccaattaaca acacacatat ccaccacaga cagaagagat cagtgagcat tgaacggttt     300
gtggagacat tggtagtggc agacaaaatg atggtgggct accatggccg caagacatt      360
gaacattaca ttttgagtgt gatgaatatt gttgccaaac tttaccgtga ttccagccta     420
ggaaacgttg tgaatattat agtggcccgc ttaattgttc tcacagaaga tcagccaaac     480
ttggagataa accaccatgc agacaagtcc ctcgatagct tctgtaaatg cagaaatcc      540
attctctccc accaaagtga tggaaacacc attccagaaa atgggattgc ccaccacgat     600
aatgcagttc ttattactag atatgatatc tgcacttata aaaataagcc ctgtggaaca     660
ctgggcttgg cctctgtggc tggaatgtgt gagcctgaaa ggagctgcag cattaatgaa     720
gacattggcc tgggttcagc ttttaccatt gcacatgaga ttggtcacaa ttttggtatg     780
aaccatgatg gaattggaaa tcttgtgggg acgaaaggtc atgaagcagc aaaacttatg     840
gcagctcaca ttactgcgaa taccaatcct ttttcctggt ctgcttgcag tcgagactac     900
atcaccagct ttctagaatt tcttaaactc ggtgattcaa taagtggttc atga           954
```

<210> SEQ ID NO 16
<211> LENGTH: 317
<212> TYPE: PRT
<213> ORGANISM: Homo sapiens

<400> SEQUENCE: 16

```
Met Lys Thr His Gly Val Ile Ala Thr Glu Asp Glu Tyr Phe Ile
1               5                   10                  15

Glu Pro Leu Lys Asn Thr Thr Glu Asp Ser Lys His Phe Ser Tyr Glu
            20                  25                  30

Asn Gly His Pro His Val Ile Tyr Lys Lys Ser Ala Leu Gln Gln Arg
        35                  40                  45

His Leu Tyr Asp His Ser His Cys Gly Val Ser Asp Phe Thr Arg Ser
    50                  55                  60

Gly Lys Pro Trp Trp Leu Asn Asp Thr Ser Thr Val Ser Tyr Ser Leu
65                  70                  75                  80

Pro Ile Asn Asn Thr His Ile His His Arg Gln Lys Arg Ser Val Ser
                85                  90                  95

Ile Glu Arg Phe Val Glu Thr Leu Val Val Ala Asp Lys Met Met Val
            100                 105                 110

Gly Tyr His Gly Arg Lys Asp Ile Glu His Tyr Ile Leu Ser Val Met
        115                 120                 125

Asn Ile Val Ala Lys Leu Tyr Arg Asp Ser Ser Leu Gly Asn Val Val
    130                 135                 140

Asn Ile Ile Val Ala Arg Leu Ile Val Leu Thr Glu Asp Gln Pro Asn
145                 150                 155                 160

Leu Glu Ile Asn His His Ala Asp Lys Ser Leu Asp Ser Phe Cys Lys
                165                 170                 175

Trp Gln Lys Ser Ile Leu Ser His Gln Ser Asp Gly Asn Thr Ile Pro
            180                 185                 190

Glu Asn Gly Ile Ala His His Asp Asn Ala Val Leu Ile Thr Arg Tyr
        195                 200                 205

Asp Ile Cys Thr Tyr Lys Asn Lys Pro Cys Gly Thr Leu Gly Leu Ala
    210                 215                 220

Ser Val Ala Gly Met Cys Glu Pro Glu Arg Ser Cys Ser Ile Asn Glu
225                 230                 235                 240

Asp Ile Gly Leu Gly Ser Ala Phe Thr Ile Ala His Glu Ile Gly His
                245                 250                 255

Asn Phe Gly Met Asn His Asp Gly Ile Gly Asn Ser Cys Gly Thr Lys
            260                 265                 270

Gly His Glu Ala Ala Lys Leu Met Ala Ala His Ile Thr Ala Asn Thr
        275                 280                 285

Asn Pro Phe Ser Trp Ser Ala Cys Ser Arg Asp Tyr Ile Thr Ser Phe
    290                 295                 300

Leu Glu Phe Leu Lys Leu Gly Asp Ser Ile Ser Gly Ser
305                 310                 315
```

<210> SEQ ID NO 17
<211> LENGTH: 480
<212> TYPE: DNA
<213> ORGANISM: Homo sapiens

<400> SEQUENCE: 17

```
atgaaaacgc atggtgttat tgctacagaa gatgaagagt attttatcga acctttaaag      60
aataccacag aggattccaa gcatttagt tatgaaaatg gccaccctca tgttattac       120 aaaagtctg cccttcaaca cgacatctg tatgatcact ctcattgtgg ggtttcggat       180
ttcacaagaa gtggcaaacc ttggtggctg aatgacacat ccactgtttc ttattcacta     240
ccaattaaca acacacatat ccaccacaga cagaagagat cagtgagcat tgaacgtttt    300
gtggagacat tggtagtggc agacaaaatg atggtgggct accatggccg caaagacatt    360
```

```
gaacattaca ttttgagtgt gatgaatatt gttgccaaac tttaccgtga ttccagccta    420
ggaaacgttg tgaatattat agtggcccgc ttaattgttc tcacagaaga tcagatatga    480
```

<210> SEQ ID NO 18
<211> LENGTH: 159
<212> TYPE: PRT
<213> ORGANISM: Homo sapiens

<400> SEQUENCE: 18

```
Met Lys Thr His Gly Val Ile Ala Thr Glu Asp Glu Glu Tyr Phe Ile
  1               5                  10                  15

Glu Pro Leu Lys Asn Thr Thr Glu Asp Ser Lys His Phe Ser Tyr Glu
                 20                  25                  30

Asn Gly His Pro His Val Ile Tyr Lys Lys Ser Ala Leu Gln Gln Arg
             35                  40                  45

His Leu Tyr Asp His Ser His Cys Gly Val Ser Asp Phe Thr Arg Ser
         50                  55                  60

Gly Lys Pro Trp Trp Leu Asn Asp Thr Ser Thr Val Ser Tyr Ser Leu
 65                  70                  75                  80

Pro Ile Asn Asn Thr His Ile His His Arg Gln Lys Arg Ser Val Ser
                 85                  90                  95

Ile Glu Arg Phe Val Glu Thr Leu Val Val Ala Asp Lys Met Met Val
                100                 105                 110

Gly Tyr His Gly Arg Lys Asp Ile Glu His Tyr Ile Leu Ser Val Met
            115                 120                 125

Asn Ile Val Ala Lys Leu Tyr Arg Asp Ser Ser Leu Gly Asn Val Val
        130                 135                 140

Asn Ile Ile Val Ala Arg Leu Ile Val Leu Thr Glu Asp Gln Ile
145                 150                 155
```

<210> SEQ ID NO 19
<211> LENGTH: 1071
<212> TYPE: DNA
<213> ORGANISM: Homo sapiens

<400> SEQUENCE: 19

```
atgaaaacgc atggtgttat tgctacagaa gatgaagagt attttatcga acctttaaag     60
aataccacag aggattccaa gcattttagt tatgaaaatg gccaccctca tgttatttac    120
aaaaagtctg cccttcaaca acgacatctg tatgatcact ctcattgtgg ggtttcggat    180
ttcacaagaa gtggcaaacc ttggtggctg aatgacacat ccactgtttc ttattcacta    240
ccaattaaca cacacatat ccaccacaga cagaagagat cagtgagcat tgaacggttt    300
gtggagacat tggtagtggc agacaaaatg atggtgggct accatggccg caaagacatt    360
gaacattaca ttttgagtgt gatgaatatt gttgccaaac tttaccgtga ttccagccta    420
ggaaacgttg tgaatattat agtggcccgc ttaattgttc tcacagaaga tcagccaaac    480
ttggagataa accaccatgc agacaagtcc ctcgatagct tctgtaaatg cagaaatcc    540 attctctccc accaaagtga tggaaacacc attccagaaa atgggattgc ccaccacgat    600
aatgcagttc ttattactag atatgatatc tgcacttata aaaataagcc ctgtggaaca    660
ctgggcttgg cctctgtggc tggaatgtgt gagcctgaaa ggagctgcag cattaatgaa    720
gacattggcc tgggttcagc ttttaccatt gcacatgaga ttggtcacaa ttttggtatg    780
aaccatgatg gaattggaaa tccttgtggg acgaaaggtc atgaagcagc aaaacttatg    840
```

```
gcagctcaca ttactgcgaa taccaatcct ttttcctggt ctgcttgcag tcgagactac    900
atcaccagct ttctagattc aggccgtggt acttgccttg ataatgagcc tcccaagcgt    960
gactttcttt atccagctgt ggccccaggt caggtgtatg atgctgatga gcaatgtcgt   1020
ttccagtatg gagcaacctc ccgccaatgt aaatatgggg tctttagata a             1071
```

<210> SEQ ID NO 20
<211> LENGTH: 356
<212> TYPE: PRT
<213> ORGANISM: Homo sapiens

<400> SEQUENCE: 20

```
Met Lys Thr His Gly Val Ile Ala Thr Glu Asp Glu Tyr Phe Ile
 1               5                  10                  15

Glu Pro Leu Lys Asn Thr Thr Glu Asp Ser Lys His Phe Ser Tyr Glu
                20                  25                  30

Asn Gly His Pro His Val Ile Tyr Lys Lys Ser Ala Leu Gln Gln Arg
             35                  40                  45

His Leu Tyr Asp His Ser His Cys Gly Val Ser Asp Phe Thr Arg Ser
 50                  55                  60

Gly Lys Pro Trp Trp Leu Asn Asp Thr Ser Thr Val Ser Tyr Ser Leu
 65                  70                  75                  80

Pro Ile Asn Asn Thr His Ile His His Arg Gln Lys Arg Ser Val Ser
                 85                  90                  95

Ile Glu Arg Phe Val Glu Thr Leu Val Val Ala Asp Lys Met Met Val
                100                 105                 110

Gly Tyr His Gly Arg Lys Asp Ile Glu His Tyr Ile Leu Ser Val Met
            115                 120                 125

Asn Ile Val Ala Lys Leu Tyr Arg Asp Ser Ser Leu Gly Asn Val Val
130                 135                 140

Asn Ile Ile Val Ala Arg Leu Ile Val Leu Thr Glu Asp Gln Pro Asn
145                 150                 155                 160

Leu Glu Ile Asn His His Ala Asp Lys Ser Leu Asp Ser Phe Cys Lys
                165                 170                 175

Trp Gln Lys Ser Ile Leu Ser His Gln Ser Asp Gly Asn Thr Ile Pro
            180                 185                 190

Glu Asn Gly Ile Ala His His Asp Asn Ala Val Leu Ile Thr Arg Tyr
        195                 200                 205

Asp Ile Cys Thr Tyr Lys Asn Lys Pro Cys Gly Thr Leu Gly Leu Ala
210                 215                 220

Ser Val Ala Gly Met Cys Glu Pro Glu Arg Ser Cys Ser Ile Asn Glu
225                 230                 235                 240

Asp Ile Gly Leu Gly Ser Ala Phe Thr Ile Ala His Glu Ile Gly His
                245                 250                 255

Asn Phe Gly Met Asn His Asp Gly Ile Gly Asn Ser Cys Gly Thr Lys
            260                 265                 270

Gly His Glu Ala Ala Lys Leu Met Ala Ala His Ile Thr Ala Asn Thr
        275                 280                 285

Asn Pro Phe Ser Trp Ser Ala Cys Ser Arg Asp Tyr Ile Thr Ser Phe
    290                 295                 300

Leu Asp Ser Gly Arg Gly Thr Cys Leu Asp Asn Glu Pro Pro Lys Arg
305                 310                 315                 320

Asp Phe Leu Tyr Pro Ala Val Ala Pro Gly Gln Val Tyr Asp Ala Asp
                325                 330                 335
```

```
Glu Gln Cys Arg Phe Gln Tyr Gly Ala Thr Ser Arg Gln Cys Lys Tyr
            340                 345                 350

Gly Val Phe Arg
        355
```

<210> SEQ ID NO 21
<211> LENGTH: 1317
<212> TYPE: DNA
<213> ORGANISM: Homo sapiens

<400> SEQUENCE: 21

| | | | | | |
|---|---|---|---|---|---|
| atgaaaacgc | atggtgttat | tgctacagaa | gatgaagagt | attttatcga | acctttaaag    60 |
| aataccacag | aggattccaa | gcattttagt | tatgaaaatg | gccaccctca | tgttatttac   120 |
| aaaaagtctg | cccttcaaca | acgacatctg | tatgatcact | ctcattgtgg | ggtttcggat   180 |
| ttcacaagaa | gtggcaaacc | ttggtggctg | aatgacacat | ccactgtttc | ttattcacta   240 |
| ccaattaaca | acacacatat | ccaccacaga | cagaagagat | cagtgagcat | tgaacggttt   300 |
| gtggagacat | tggtagtggc | agacaaaatg | atggtgggct | accatggccg | caaagacatt   360 |
| gaacattaca | ttttgagtgt | gatgaatatt | gttgccaaac | tttaccgtga | ttccagccta   420 |
| ggaaacgttg | tgaatattat | agtggcccgc | ttaattgttc | tcacagaaga | tcagccaaac   480 |
| ttggagataa | accaccatgc | agacaagtcc | ctcgatagcc | tctgtaaatg | cagaaatcc    540 |
| attctctccc | accaaagtga | tggaaacacc | attccagaaa | atgggattgc | ccaccacgat   600 |
| aatgcagttc | ttattactag | atatgatatc | tgcacttata | aaaataagcc | ctgtggaaca   660 |
| ctgggcttgg | cctctgtggc | tggaatgtgt | gagcctgaaa | ggagctgcag | cattaatgaa   720 |
| gacattggcc | tgggttcagc | ttttaccatt | gcacatgaga | ttggtcacaa | ttttggtatg   780 |
| aaccatgatg | gaattggaaa | tcttgtgggg | acgaaaggtc | atgaagcagc | aaaacttatg   840 |
| gcagctcaca | ttactgcgaa | taccaatcct | ttttcctggt | ctgcttgcag | tcgagactac   900 |
| atcaccagct | ttctagattc | aggccgtggt | acttgccttg | ataatgagcc | tcccaagcgt   960 |
| gactttcttt | atccagctgt | ggccccaggt | caggtgtatg | atgctgatga | gcaatgtcgt  1020 |
| ttccagtatg | gagcaaccct | ccgccaatgt | aaatatgggg | aagtgtgtag | agagctctgg  1080 |
| tgtctcagca | aaagcaaccg | ctgtgtcacc | aacagtattc | cagcagctga | ggggacactg  1140 |
| tgtcaaactg | gaatattga  | aaaagggtgg | tgttatcagg | gagattgtgt | tccttttggc  1200 |
| acttggcccc | agagcataga | tggggctgg  | ggtccctggt | cactatgggg | agagtgcagc  1260 |
| aggacctgcg | ggggaggcgt | ctcctcatcc | ctaagacact | gtgacagtcc | agcgtaa     1317 |

<210> SEQ ID NO 22
<211> LENGTH: 438
<212> TYPE: PRT
<213> ORGANISM: Homo sapiens

<400> SEQUENCE: 22

```
Met Lys Thr His Gly Val Ile Ala Thr Glu Asp Glu Glu Tyr Phe Ile
  1               5                  10                  15

Glu Pro Leu Lys Asn Thr Thr Glu Asp Ser Lys His Phe Ser Tyr Glu
             20                  25                  30

Asn Gly His Pro His Val Ile Tyr Lys Lys Ser Ala Leu Gln Gln Arg
         35                  40                  45

His Leu Tyr Asp His Ser His Cys Gly Val Ser Asp Phe Thr Arg Ser
     50                  55                  60

Gly Lys Pro Trp Trp Leu Asn Asp Thr Ser Thr Val Ser Tyr Ser Leu
```

```
                65                  70                  75                  80
Pro Ile Asn Asn Thr His Ile His His Arg Gln Lys Arg Ser Val Ser
                    85                  90                  95
Ile Glu Arg Phe Val Glu Thr Leu Val Val Ala Asp Lys Met Met Val
                100                 105                 110
Gly Tyr His Gly Arg Lys Asp Ile Glu His Tyr Ile Leu Ser Val Met
            115                 120                 125
Asn Ile Val Ala Lys Leu Tyr Arg Asp Ser Ser Leu Gly Asn Val Val
        130                 135                 140
Asn Ile Ile Val Ala Arg Leu Ile Val Leu Thr Glu Asp Gln Pro Asn
145                 150                 155                 160
Leu Glu Ile Asn His His Ala Asp Lys Ser Leu Asp Ser Phe Cys Lys
                165                 170                 175
Trp Gln Lys Ser Ile Leu Ser His Gln Ser Asp Gly Asn Thr Ile Pro
                180                 185                 190
Glu Asn Gly Ile Ala His His Asp Asn Ala Val Leu Ile Thr Arg Tyr
            195                 200                 205
Asp Ile Cys Thr Tyr Lys Asn Lys Pro Cys Gly Thr Leu Gly Leu Ala
        210                 215                 220
Ser Val Ala Gly Met Cys Glu Pro Glu Arg Ser Cys Ser Ile Asn Glu
225                 230                 235                 240
Asp Ile Gly Leu Gly Ser Ala Phe Thr Ile Ala His Glu Ile Gly His
                245                 250                 255
Asn Phe Gly Met Asn His Asp Gly Ile Gly Asn Ser Cys Gly Thr Lys
                260                 265                 270
Gly His Glu Ala Ala Lys Leu Met Ala Ala His Ile Thr Ala Asn Thr
            275                 280                 285
Asn Pro Phe Ser Trp Ser Ala Cys Ser Arg Asp Tyr Ile Thr Ser Phe
        290                 295                 300
Leu Asp Ser Gly Arg Gly Thr Cys Leu Asp Asn Glu Pro Pro Lys Arg
305                 310                 315                 320
Asp Phe Leu Tyr Pro Ala Val Ala Pro Gly Gln Val Tyr Asp Ala Asp
                325                 330                 335
Glu Gln Cys Arg Phe Gln Tyr Gly Ala Thr Ser Arg Gln Cys Lys Tyr
                340                 345                 350
Gly Glu Val Cys Arg Glu Leu Trp Cys Leu Ser Lys Ser Asn Arg Cys
            355                 360                 365
Val Thr Asn Ser Ile Pro Ala Ala Glu Gly Thr Leu Cys Gln Thr Gly
        370                 375                 380
Asn Ile Glu Lys Gly Trp Cys Tyr Gln Gly Asp Cys Val Pro Phe Gly
385                 390                 395                 400
Thr Trp Pro Gln Ser Ile Asp Gly Gly Trp Gly Pro Trp Ser Leu Trp
                405                 410                 415
Gly Glu Cys Ser Arg Thr Cys Gly Gly Val Ser Ser Ser Leu Arg
                420                 425                 430
His Cys Asp Ser Pro Ala
            435

<210> SEQ ID NO 23
<211> LENGTH: 2274
<212> TYPE: DNA
<213> ORGANISM: Homo sapiens

<400> SEQUENCE: 23
```

-continued

```
atgaaaacgc atggtgttat tgctacagaa gatgaagagt attttatcga acctttaaag    60
aataccacag aggattccaa gcattttagt tatgaaaatg gccaccctca tgttatttac   120
aaaaagtctg cccttcaaca acgacatctg tatgatcact ctcattgtgg ggtttcggat   180
ttcacaagaa gtggcaaacc ttggtggctg aatgacacat ccactgtttc ttattcacta   240
ccaattaaca acacacatat ccaccacaga cagaagagat cagtgagcat tgaacggttt   300
gtggagacat tggtagtggc agacaaaatg atggtgggct accatggccg caaagacatt   360
gaacattaca ttttgagtgt gatgaatatt gttgccaaac tttaccgtga ttccagccta   420
ggaaacgttg tgaatattat agtggcccgc ttaattgttc tcacagaaga tcagccaaac   480
ttggagataa accaccatgc agacaagtcc ctcgatagct tctgtaaatg cagaaatcc    540
attctctccc accaaagtga tggaaacacc attccagaaa atgggattgc ccaccacgat   600
aatgcagttc ttattactag atatgatatc tgcacttata aaataagcc ctgtggaaca    660
ctgggcttgg cctctgtggc tggaatgtgt gagcctgaaa ggagctgcag cattaatgaa   720
gacattggcc tgggttcagc ttttaccatt gcacatgaga ttggtcacaa ttttggtatg   780
aaccatgatg gaattggaaa tcttgtgggg acgaaaggtc atgaagcagc aaaacttatg   840
gcagctcaca ttactgcgaa taccaatcct ttttcctggt ctgcttgcag tcgagactac   900
atcaccagct ttctagattc aggccgtggt acttgccttg ataatgagcc tcccaagcgt   960
gactttcttt atccagctgt ggccccaggt caggtgtatg atgctgatga gcaatgtcgt  1020
ttccagtatg gagcaacctc ccgccaatgt aaatatgggg aagtgtgtag agagctctgg  1080
tgtctcagca aaagcaaccg ctgtgtcacc aacagtattc cagcagctga ggggacactg  1140
tgtcaaactg gaatattga aaagggtgg tgttatcagg gagattgtgt ccttttggc    1200
acttggcccc agagcataga tggggctgg ggtccctggt cactatgggg agagtgcagc   1260
aggacctgcg ggggaggcgt ctcctcatcc ctaagacact gtgacagtcc agcaccttca   1320
ggaggtggaa aatattgcct tggggaaagg aaacggtatc gctcctgtaa cacagatcca  1380
tgccctttgg gttcccgaga ttttcgagag aaacagtgtg cagactttga caatatgcct  1440
ttccgaggaa agtattataa ctggaaaccc tatactggag gtgggtaaa ccttgtgca    1500
ttaaactgct tggctgaagg ttataatttc tacactgaac gtgctcctgc ggtgatcgat  1560
gggacccagt gcaatgcgga ttcactggat atctgcatca atggagaatg caagcacgta  1620
ggctgtgata atatttgg atctgatgct agggaagata gatgtcgagt ctgtggaggg    1680
gacggaagca catgtgatgc cattgaaggg ttcttcaatg attcactgcc caggggaggc  1740
tacatggaag tggtgcagat accaagaggc tctgttcaca ttgaagttag agaagttgcc  1800
atgtcaaaga actatattgc tttaaaatct gaaggagatg attactatat taatggtgcc  1860
tggactattg actggcctag gaaatttgat gttgctggga cagcttttca ttacaagaga  1920
ccaactgatg aaccagaatc cttggaagct ctaggtccta cctcagaaaa tctcatcgtc  1980
atggttctgc ttcaagaaca gaatttggga attaggtata agttcaatgt tcccatcact  2040
cgaactggcg gtgagataa tgaagttggc tttacatgga atcatcagcc ttggtcagaa   2100
tgctcagcta cttgtgctgg aggtaagatg cccactaggc agcccaccca gagggcaaga  2160
tggagaacaa aacacattct gagctatgct ttgtgttttgt taaaaagct aattggaaac   2220
atttcttgca ggtttgcttc aagctgtaat ttagcaaaag aaactttgct ttaa         2274
```

<210> SEQ ID NO 24
<211> LENGTH: 757

```
<212> TYPE: PRT
<213> ORGANISM: Homo sapiens

<400> SEQUENCE: 24

Met Lys Thr His Gly Val Ile Ala Thr Glu Asp Glu Tyr Phe Ile
  1               5                  10                  15

Glu Pro Leu Lys Asn Thr Thr Glu Asp Ser Lys His Phe Ser Tyr Glu
             20                  25                  30

Asn Gly His Pro His Val Ile Tyr Lys Lys Ser Ala Leu Gln Gln Arg
         35                  40                  45

His Leu Tyr Asp His Ser His Cys Gly Val Ser Asp Phe Thr Arg Ser
 50                  55                  60

Gly Lys Pro Trp Trp Leu Asn Asp Thr Ser Thr Val Ser Tyr Ser Leu
 65                  70                  75                  80

Pro Ile Asn Asn Thr His Ile His His Arg Gln Lys Arg Ser Val Ser
                 85                  90                  95

Ile Glu Arg Phe Val Glu Thr Leu Val Val Ala Asp Lys Met Met Val
            100                 105                 110

Gly Tyr His Gly Arg Lys Asp Ile Glu His Tyr Ile Leu Ser Val Met
        115                 120                 125

Asn Ile Val Ala Lys Leu Tyr Arg Asp Ser Ser Leu Gly Asn Val Val
130                 135                 140

Asn Ile Ile Val Ala Arg Leu Ile Val Leu Thr Glu Asp Gln Pro Asn
145                 150                 155                 160

Leu Glu Ile Asn His His Ala Asp Lys Ser Leu Asp Ser Phe Cys Lys
                165                 170                 175

Trp Gln Lys Ser Ile Leu Ser His Gln Ser Asp Gly Asn Thr Ile Pro
            180                 185                 190

Glu Asn Gly Ile Ala His His Asp Asn Ala Val Leu Ile Thr Arg Tyr
        195                 200                 205

Asp Ile Cys Thr Tyr Lys Asn Lys Pro Cys Gly Thr Leu Gly Leu Ala
    210                 215                 220

Ser Val Ala Gly Met Cys Glu Pro Glu Arg Ser Cys Ser Ile Asn Glu
225                 230                 235                 240

Asp Ile Gly Leu Gly Ser Ala Phe Thr Ile Ala His Glu Ile Gly His
                245                 250                 255

Asn Phe Gly Met Asn His Asp Gly Ile Gly Asn Ser Cys Gly Thr Lys
            260                 265                 270

Gly His Glu Ala Ala Lys Leu Met Ala Ala His Ile Thr Ala Asn Thr
        275                 280                 285

Asn Pro Phe Ser Trp Ser Ala Cys Ser Arg Asp Tyr Ile Thr Ser Phe
    290                 295                 300

Leu Asp Ser Gly Arg Gly Thr Cys Leu Asp Asn Glu Pro Pro Lys Arg
305                 310                 315                 320

Asp Phe Leu Tyr Pro Ala Val Ala Pro Gly Gln Val Tyr Asp Ala Asp
                325                 330                 335

Glu Gln Cys Arg Phe Gln Tyr Gly Ala Thr Ser Arg Gln Cys Lys Tyr
            340                 345                 350

Gly Glu Val Cys Arg Glu Leu Trp Cys Leu Ser Lys Ser Asn Arg Cys
        355                 360                 365

Val Thr Asn Ser Ile Pro Ala Ala Glu Gly Thr Leu Cys Gln Thr Gly
    370                 375                 380

Asn Ile Glu Lys Gly Trp Cys Tyr Gln Gly Asp Cys Val Pro Phe Gly
385                 390                 395                 400
```

```
Thr Trp Pro Gln Ser Ile Asp Gly Gly Trp Gly Pro Trp Ser Leu Trp
                405                 410                 415
Gly Glu Cys Ser Arg Thr Cys Gly Gly Gly Val Ser Ser Ser Leu Arg
            420                 425                 430
His Cys Asp Ser Pro Ala Pro Ser Gly Gly Lys Tyr Cys Leu Gly
        435                 440                 445
Glu Arg Lys Arg Tyr Arg Ser Cys Asn Thr Asp Pro Cys Pro Leu Gly
    450                 455                 460
Ser Arg Asp Phe Arg Glu Lys Gln Cys Ala Asp Phe Asp Asn Met Pro
465                 470                 475                 480
Phe Arg Gly Lys Tyr Tyr Asn Trp Lys Pro Tyr Thr Gly Gly Gly Val
                485                 490                 495
Lys Pro Cys Ala Leu Asn Cys Leu Ala Glu Gly Tyr Asn Phe Tyr Thr
            500                 505                 510
Glu Arg Ala Pro Ala Val Ile Asp Gly Thr Gln Cys Asn Ala Asp Ser
        515                 520                 525
Leu Asp Ile Cys Ile Asn Gly Glu Cys Lys His Val Gly Cys Asp Asn
    530                 535                 540
Ile Leu Gly Ser Asp Ala Arg Glu Asp Arg Cys Arg Val Cys Gly Gly
545                 550                 555                 560
Asp Gly Ser Thr Cys Asp Ala Ile Glu Gly Phe Phe Asn Asp Ser Leu
                565                 570                 575
Pro Arg Gly Gly Tyr Met Glu Val Val Gln Ile Pro Arg Gly Ser Val
            580                 585                 590
His Ile Glu Val Arg Glu Val Ala Met Ser Lys Asn Tyr Ile Ala Leu
        595                 600                 605
Lys Ser Glu Gly Asp Asp Tyr Tyr Ile Asn Gly Ala Trp Thr Ile Asp
    610                 615                 620
Trp Pro Arg Lys Phe Asp Val Ala Gly Thr Ala Phe His Tyr Lys Arg
625                 630                 635                 640
Pro Thr Asp Glu Pro Glu Ser Leu Glu Ala Leu Gly Pro Thr Ser Glu
                645                 650                 655
Asn Leu Ile Val Met Val Leu Leu Gln Glu Gln Asn Leu Gly Ile Arg
            660                 665                 670
Tyr Lys Phe Asn Val Pro Ile Thr Arg Thr Gly Ser Gly Asp Asn Glu
        675                 680                 685
Val Gly Phe Thr Trp Asn His Gln Pro Trp Ser Glu Cys Ser Ala Thr
    690                 695                 700
Cys Ala Gly Gly Lys Met Pro Thr Arg Gln Pro Thr Gln Arg Ala Arg
705                 710                 715                 720
Trp Arg Thr Lys His Ile Leu Ser Tyr Ala Leu Cys Leu Leu Lys Lys
                725                 730                 735
Leu Ile Gly Asn Ile Ser Cys Arg Phe Ala Ser Ser Cys Asn Leu Ala
            740                 745                 750
Lys Glu Thr Leu Leu
        755

<210> SEQ ID NO 25
<211> LENGTH: 3160
<212> TYPE: DNA
<213> ORGANISM: Homo sapiens

<400> SEQUENCE: 25
aatcatccag ttttctaaat tatggaaatt ttgtggaaga cgttgacctg gattttgagc      60
```

-continued

```
ctcatcatgg cttcatcgga atttcatagt gaccacaggc tttcatacag ttctcaagag    120
gaattcctga cttatcttga acactaccag ctaactattc aataagggt tgatcaaaat     180
ggagcatttc tcagctttac tgtgaaaaat gataaacact caaggagaag acggagtatg    240
gaccctattg atccacagca ggcagtatct aagttatttt ttaaactttc agcctatggc    300
aagcactttc atctaaactt gactctcaac acagattttg tgtccaaaca ttttacagta    360
gaatattggg ggaaagatgg acccagtgg aaacatgatt ttttagacaa ctgtcattac     420
acaggatatt tgcaagatca acgtagtaca actaaagtgg ctttaagcaa ctgtgttggg    480
ttggaaaagc tgccaaaatt ttctcctgct gcaattcaag ttggctgggg gccgaatttg    540
aagatgaaaa cgcatggtgt tattgctaca aagatgaag agtattttat cgaaccttta    600
aagaatacca cagaggattc caagcatttt agttatgaaa atggccaccc tcatgttatt    660
tacaaaaagt ctgcccttca acaacgacat ctgtatgatc actctcattg tggggtttcg    720
gatttcacaa gaagtggcaa accttggtgg ctgaatgaca catccactgt ttcttattca    780
ctaccaatta acaacacaca tatccaccac agacagaaga gatcagtgag cattgaacgg    840
tttgtggaga cattggtagt ggcagacaaa atgatggtgg gctaccatgg ccgcaaagac    900
attgaacatt acattttgag tgtgatgaat attgtcaggt tgccaaactt taccgtgatt    960
ccagcctagg aaacgttgtg aatattatag tggcccgctt aattgttctc acagaagatc   1020
agccaaactt ggagataaac caccatgcag acaagtccct cgatagcttc tgtaaatggc   1080
agaaatccat tctctcccac caaagtgatg gaaacaccat tccagaaaat gggattgccc   1140
accacgataa tgcagttctt attactagat atgatatctg cacttataaa aataagccct   1200
gtggaacact gggcttggcc tctgtggctg gaatgtgtga gcctgaaagg agctgcagca   1260
ttaatgaaga cattggcctg ggttcagctt ttaccattgc acatgagatt ggtcacaatt   1320
ttggtatgaa ccatgatgga attggaaatt cttgtgggac gaaaggtcat gaagcagcaa   1380
aacttatggc agctcacatt actgcgaata ccaatccttt ttcctggtct gcttgcagtc   1440
gagactacat caccagcttt ctagaatttc ttaaactcgg tgattcaata agtggttcat   1500
gaatcgccca gaagccgtcc tgattaaata ataaagaacc catttccgtt aaaatggacg   1560
tgttatgcca gcttctgatg ttttccggcg acggctttgc agttcaggcc gtggtacttg   1620
ccttgataat gagcctccca agcgtgactt tctttatcca gctgtggccc caggtcaggt   1680
gtatgatgct gatgagcaat gtcgtttcca gtatggagca acctcccgcc aatgtaaata   1740
tggggtcttt agataataac tctttcaacc aactgccaat cagaaaatct tctactccat   1800
ctatgacctg gaactcccca ccccttaaaa tgtataaaac caagctgtag cctgaccacc   1860
ttgggcatat gttcttagga tctcaagtgt gtagagagct ctggtgtctc agcaaaagca   1920
accgctgtgt caccaacagt attccagcag ctgaggggac actgtgtcaa actgggaata   1980
ttgaaaaagg gtggtgttat cagggagatt gtgttccttt tggcacttgg ccccagagca   2040
tagatggggg ctggggtccc tggtcactat ggggagagtg cagcaggacc tgcgggggag   2100
gcgtctcctc atccctaaga cactgtgaca gtccagcacg taagtagcta aaaccttcag   2160
gaggtggaaa atattgcctt ggggaaagga acggtatcg ctcctgtaac acagatccat    2220
gccctttggg ttcccgagat tttcgagaga acagtgtgc agactttgac aatatgcctt    2280
tccgaggaaa gtattataac tggaaaccct atactggagg tggggtaaaa ccttgtgcat   2340
taaactgctt ggctgaaggt tataatttct acactgaacg tgctcctgcg gtgatcgatg   2400
```

```
ggacccagtg caatgcggat tcactggata tctgcatcaa tggagaatgc aagcacgtag    2460
gctgtgataa tattttggga tctgatgcta gggaagatag atgtcgagtc tgtggagggg    2520
acggaagcac atgtgatgcc attgaagggt tcttcaatga ttcactgccc agggaggct    2580 acatggaagt ggtgcagata ccaagaggct ctgttcacat tgaagttaga gaagttgcca    2640
tgtcaaagaa ctatattgct ttaaaatctg aaggagatga ttactatatt aatggtgcct    2700
ggactattga ctggcctagg aaatttgatg ttgctgggac agcttttcat tacaagagac    2760
caactgatga accagaatcc ttggaagctc taggtcctac ctcagaaaat ctcatcgtca    2820
tggttctgct tcaagaacag aatttgggaa ttaggtataa gttcaatgtt cccatcactc    2880
gaactggcag tggagataat gaagttggct ttacatggaa tcatcagcct tggtcagaat    2940
gctcagctac ttgtgctgga ggtaagatgc ccactaggca gcccacccag agggcaagat    3000
ggagaacaaa acacattctg agctatgctt tgtgtttgtt aaaaaagcta attggaaaca    3060
tttcttgcag gtttgcttca agctgtaatt tagcaaaaga aactttgctt taattatatt    3120
atattccatt tgttttcaac ctcatgtaat ttgtgcagat                          3160
```

HUMAN PROTEASES AND POLYNUCLEOTIDES ENCODING THE SAME

The present application is a continuation of U.S. application Ser. No. 09/963,791, now U.S. Pat. No. 6,649,399, filed Dec. 8, 2000, which claims the benefit of U.S. Provisional Application No. 60/169,769 which was filed on Dec. 9, 1999 each of which are herein incorporated by reference in their entirety.

1. INTRODUCTION

The present invention relates to the discovery, identification, and characterization of novel human polynucleotides encoding proteins sharing sequence similarity with mammalian proteases. The invention encompasses the described polynucleotides, host cell expression systems, the encoded protein, fusion proteins, polypeptides and peptides, antibodies to the encoded proteins and peptides, and genetically engineered animals that either lack or over express the disclosed sequences, antagonists and agonists of the proteins, and other compounds that modulate the expression or activity of the proteins encoded by the disclosed polynucleotides that can be used for diagnosis, drug screening, clinical trial monitoring and the treatment of physiological disorders.

2. BACKGROUND OF THE INVENTION

Proteases cleave protein substrates as part of degradation, maturation, and secretory pathways within the body. Proteases have been associated with, inter alia, regulating development, modulating cellular processes, and infectious disease.

3. SUMMARY OF THE INVENTION

The present invention relates to the discovery, identification, and characterization of nucleotides that encode a novel human protein, and the corresponding amino acid sequence of this proteins. The novel human protein (NHP) described for the first time herein shares structural similarity with animal proteases, and particularly metalloproteinases such as ADAM-TS6, a zinc metalloproteinase (Hurskainen et al., 1999, J. Biol Chem. 274(36):25555–63). However this NHP contains additional regions (exons) that make it unique.

The novel human nucleic acid (cDNA) sequences described herein, encode a proteins/open reading frames (ORFs) of 908, 292, 468, 310, 507, 589, 141, 317, 159, 356, 438, and 757 amino acids in length (see SEQ ID NOS: 2, 4, 6, 8, 10, 12, 14, 16, 18, 20, 22, and 24).

The invention also encompasses agonists and antagonists of the described NHP, including small molecules, large molecules, mutant NHPs, or portions thereof that compete with native NHP, peptides, and antibodies, as well as nucleotide sequences that can be used to inhibit the expression of the described NHP (e.g., antisense and ribozyme molecules, and gene or regulatory sequence replacement constructs) or to enhance the expression of the described NHP (e.g., expression constructs that place the described sequence under the control of a strong promoter system), and transgenic animals that express a NHP transgene, or "knockouts" (which can be conditional) that do not express a functional NHP.

Further, the present invention also relates to processes for identifying compounds that modulate, i.e., act as agonists or antagonists, of NHP expression and/or NHP activity that utilize purified preparations of the described NHP and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING

The Sequence Listing provides the sequences of the NHP ORFs encoding the described NHP amino acid sequences. SEQ ID NO: 25 describes an ORF with flanking sequences.

5. DETAILED DESCRIPTION OF THE INVENTION

The NHPs, described for the first time herein, are novel proteins that are expressed in, inter alia, human cell lines, and human fetal brain, brain, thymus, spleen, lymph node, trachea, kidney, fetal liver, testis, thyroid, adrenal gland, stomach, small intestine, uterus, placenta, adipose, esophagus, bladder, cervix, rectum, pericardium, ovary, and fetal lung cells.

The described sequences were compiled from gene trapped cDNAs and clones isolated from human testis and placenta cDNA libraries (Edge Biosystems, Gaithersburg, Md.). The present invention encompasses the nucleotides presented in the Sequence Listing, host cells expressing such nucleotides, the expression products of such nucleotides, and: (a) nucleotides that encode mammalian homologs of the described sequences, including the specifically described NHPs, and the NHP products; (b) nucleotides that encode one or more portions of a NHP that correspond to functional domains of the NHP, and the polypeptide products specified by such nucleotide sequences, including but not limited to the novel regions of any active domain(s); (c) isolated nucleotides that encode mutant versions, engineered or naturally occurring, of a described NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF), or a contiguous exon splice junction first described in the Sequence Listing, that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding a NHP ORF, or its functional equivalent, encoded by a polynucleotide sequence that is about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–25 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–25, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–25 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–25.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described GTS polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–25 provides detailed information about transcriptional changes involved in a specific pathway, potentially leading to the identification of novel components or gene functions that manifest themselves as novel phenotypes.

Probes consisting of sequences first disclosed in SEQ ID NOS:1–25 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–25 can be utilized in microarrays or other assay formats, to screen collections of genetic material from patients who have a particular medical condition. These investigations can also be carried out using the sequences first disclosed in SEQ ID NOS:1–25 in silico and by comparing previously collected genetic databases and the disclosed sequences using computer software known to those in the art.

Thus the sequences first disclosed in SEQ ID NOS:1–25 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–25. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6xSSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP sequence antisense molecules, useful, for example, in NHP gene regulation (for and/or as antisense primers in amplification reactions of NHP nucleic acid sequences). With-respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP sequence, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the human cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and-agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as NHP peptides/domains corresponding to NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences (SEQ ID NO: 1, 3, 5, 7, 9, 11, 13, 15, 17, 19, 21, 23, and 25) and the corresponding deduced amino acid sequences of the described NHP are presented in the Sequence Listing. SEQ ID NO:25 describes the NHP ORF as well as flanking regions. The NHP nucleotides were obtained from human cDNA libraries using probes and/or primers generated from human gene trapped sequence tags. Expression analysis has provided evidence that the described NHP can be expressed a variety of human cells as well as gene trapped human cells.

5.2 NHP and NHP Polypeptides

NHPs, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequence encoded by the described NHP polynucleotides. The NHPs display initiator methionines in DNA sequence contexts consistent with a translation initiation site, and apparently does not display a consensus signal sequence which can indicate that the described NHP ORFs can be exemplary of the mature or processed forms of the NHPs as typically found in the body.

The NHP amino acid sequences of the invention include the amino acid sequences presented in the Sequence Listing as well as analogues and derivatives thereof, as well as any oligopeptide sequence of at least about 10–40, generally about 12–35, or about 16–30 amino acids in length first disclosed in the Sequence Listing. Further, corresponding NHP homologues from other species are encompassed by the invention. In fact, any NHP encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP products or NHP polypeptides are thought to be soluble or secreted molecules, the peptide or polypeptide can be recovered from the culture media. Such expression systems also encompass engineered host cells that express a NHP, or a functional equivalent, in situ. Purification or enrichment of NHP from such expression systems can be accomplished using appropriate detergents and lipid micelles and methods well known to'those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA-expression vectors containing NHP nucleotide sequences; yeast (e.g., *Saccharomyces, Pichia*) transformed with recombinant yeast expression vectors containing NHP encoding nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

Also encompassed by the present invention are novel protein constructs engineered in such a way that they facilitate transport of the NHP to the target site, to the desired organ, across the cell membrane and/or to the nucleus where the NHP can exert its function activity. This goal may be achieved by coupling of the NHP to a cytokine or other ligand that would direct the NHP to the target organ and facilitate receptor mediated transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes: A Practical Approach*, New RRC ed., Oxford University Press, New York and in U.S. Pat. Nos. 4,594,595, 5,459,127, 5,948,767 and 6,110,490 and their respective disclosures which are herein incorporated by reference in their entirety.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding the a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. A method of making a protein using a nucleic acid molecule comprising the nucleotide sequence described in SEQ ID NO: 1, said method comprising:

(1) expressing said nucleic acid molecule in a host cell, and (2) optionally isolating the expressed protein.

* * * * *